United States Patent
Delevati et al.

(10) Patent No.: US 11,267,959 B2
(45) Date of Patent: Mar. 8, 2022

(54) BIO-BASED EVA COMPOSITIONS AND ARTICLES AND METHODS THEREOF

(71) Applicant: Braskem S.A., Camaçari (BR)

(72) Inventors: Giancarlos Delevati, São Paulo (BR); Mauro Alfredo Soto Oviedo, São Paulo (BR); Fernanda Munhoz Anderle, São Paulo (BR); Omar Wandir Renck, São Paulo (BR); José Augusto Esteves Viveiro, São Paulo (BR)

(73) Assignee: Braskem S.A., Camaçari (BR)

( * ) Notice: Subject to any disclaimer, the term of this patent is extended or adjusted under 35 U.S.C. 154(b) by 161 days.

(21) Appl. No.: 16/385,767

(22) Filed: Apr. 16, 2019

(65) Prior Publication Data

US 2019/0315948 A1     Oct. 17, 2019

Related U.S. Application Data

(63) Continuation of application No. PCT/IB2019/020006, filed on Apr. 8, 2019.

(60) Provisional application No. 62/658,294, filed on Apr. 16, 2018.

(51) Int. Cl.
| | |
|---|---|
| *C08L 23/08* | (2006.01) |
| *C08J 9/10* | (2006.01) |
| *C08K 5/14* | (2006.01) |
| *C08K 5/3492* | (2006.01) |
| *C08K 5/11* | (2006.01) |
| *C07C 1/24* | (2006.01) |
| *C07C 11/04* | (2006.01) |
| *C12P 5/02* | (2006.01) |
| *C08J 9/36* | (2006.01) |

(52) U.S. Cl.
CPC ............ *C08L 23/0853* (2013.01); *C07C 1/24* (2013.01); *C08J 9/103* (2013.01); *C08J 9/104* (2013.01); *C08K 5/11* (2013.01); *C08K 5/14* (2013.01); *C08K 5/34924* (2013.01); *C07C 11/04* (2013.01); *C08J 9/36* (2013.01); *C08J 2201/026* (2013.01); *C08J 2203/02* (2013.01); *C08J 2203/04* (2013.01); *C08J 2323/08* (2013.01); *C08L 2312/00* (2013.01); *C12P 5/026* (2013.01)

(58) Field of Classification Search
CPC ... C08L 23/0853; C08L 2312/00; C08K 5/14; C08K 5/34924; C08K 5/11; C08J 9/104; C08J 9/103; C08J 2203/02; C08J 2203/04; C08J 2201/026; C08J 2323/08; C08J 9/36; C08J 9/0023; C08J 9/0061; C08J 2423/08; C07C 1/24; C07C 11/04; C07C 67/05; C07C 51/235; C07C 2521/04; C07C 51/23; C12P 5/026; C12P 7/10; Y02E 50/10; A43B 17/003; A43B 13/02

See application file for complete search history.

(56) References Cited

U.S. PATENT DOCUMENTS

| | | | |
|---|---|---|---|
| 4,396,789 A | 8/1983 | Barrocas et al. | |
| 5,840,971 A | 11/1998 | Gubelmann-Bonneau | |
| 8,835,703 B2 * | 9/2014 | Morschbacker | C12P 7/10 585/240 |
| 9,181,143 B2 | 11/2015 | do Carmo et al. | |
| 2011/0287204 A1 | 11/2011 | Devisme et al. | |

FOREIGN PATENT DOCUMENTS

| | | |
|---|---|---|
| EP | 0 376 558 A1 | 7/1990 |
| EP | 2346911 B1 | 8/2013 |
| JP | H04503964 A | 7/1992 |
| JP | 2015517358 A | 6/2015 |
| JP | 6011585 B2 | 10/2016 |
| WO | 9006859 A1 | 6/1990 |
| WO | 200001335 A1 | 1/2000 |
| WO | 2010101698 A2 | 9/2010 |
| WO | 2012102778 A1 | 8/2012 |
| WO | 2013172915 A1 | 11/2013 |
| WO | 2016/014230 A1 | 1/2016 |
| WO | 201694161 A1 | 6/2016 |
| WO | 2018041818 A1 | 3/2018 |

OTHER PUBLICATIONS

ELVAX™ 460 Ethylene Vinyl Acetate Copolymer, 1995.*
Hackmann et al., Green building blocks for biobased plastics, Mar. 2013.*
DuPont™ Elvax® EVA resins for Adhesives, Sealants and Wax Blends, 2012.*
PCT International Search Report and Written Opinion dated Jul. 8, 2019, in corresponding International Application No. PCT/IB2019/020006 (11 pages).
X. Li et al. "Selective Catalytic Oxidation of Ethanol to Acetic Acid on Dispersed Mo-V-Nb Mixed Oxides" Chemistry A European Journal, 2007,13, 9324-9330 (7 pages).
B. Jones et al. "The Production of Vinyl Acetate Monomer as a Co-Product from the Non-Catalytic Cracking of Soybean Oil" Processes, 3, Aug. 14, 2015 pp. 619-633 (15 pages).

(Continued)

*Primary Examiner* — Irina S Zemel
(74) *Attorney, Agent, or Firm* — Osha Bergman Watanabe & Burton LLP

(57) ABSTRACT

A copolymer may include ethylene and vinyl acetate, in which the ethylene is at least partially obtained from a renewable source of carbon. Embodiments may also be directed to curable polymer compositions, expandable polymer compositions, articles, cured articles, and expanded articles formed from or including such copolymers of ethylene and vinyl acetate, in which the ethylene is at least partially obtained from a renewable source of carbon. A process for producing an ethylene vinyl acetate copolymer may include polymerizing ethylene at least partially obtained from a renewable source of carbon with vinyl acetate to produce the ethylene vinyl actate copolymer.

36 Claims, 2 Drawing Sheets

(56) References Cited

OTHER PUBLICATIONS

N. Saichana et al. Abstract of "Acetic acid bacteria: A group of bacteria with versatile biotechnological applications" Biotechnology Advances, vol. 33, Issue 6, part 2, Nov. 1, 2015 (2 pages).
P. Raspor et al., "Biotechnological Applications of Acetic Acid Bacteria", Critical Reviews in Biotechnology, vol. 28, 2008, pp. 101-124 (26 pages).
Office Action issued in corresponding Japanese Application No. 2020-556975; dated Oct. 11, 2021 (15 pages).

* cited by examiner

BIO-BASED EVA COMPOSITIONS AND ARTICLES AND METHODS THEREOF

BACKGROUND

Polyolefin copolymers such as ethylene vinyl acetate (EVA) may be used to manufacture a varied range of articles, including films, molded products, foams, and the like. In general, polyolefins are widely used plastics worldwide, given their versatility in a wide range of applications. EVA may have characteristics such as high processability, low production cost, flexibility, low density and recycling possibility.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a copolymer of ethylene and vinyl acetate, in which the ethylene is at least partially obtained from a renewable source of carbon.

In another aspect, embodiments disclosed herein relate to an article prepared from the copolymer of ethylene and vinyl acetate, in which the ethylene is at least partially obtained from a renewable source of carbon.

In another aspect, embodiments disclosed herein relate to a curable polymer composition that includes a copolymer of ethylene and vinyl acetate, in which the ethylene is at least partially obtained from a renewable source of carbon, and at least a peroxide agent.

In yet another aspect, embodiments disclosed herein relate to a cured article prepared from the curable polymer composition that includes a copolymer of ethylene and vinyl acetate, in which the ethylene is at least partially obtained from a renewable source of carbon, and at least a peroxide agent.

In yet another aspect, embodiments disclosed herein relate to an expandable polymer composition that includes a copolymer of ethylene and vinyl acetate, in which the ethylene is at least partially obtained from a renewable source of carbon, and at least a blowing agent and a peroxide agent.

In another aspect, embodiments disclosed herein relate to an expanded article prepared from the expandable polymer composition that includes a copolymer of ethylene and vinyl acetate, in which the ethylene is at least partially obtained from a renewable source of carbon, and at least a blowing agent and a peroxide agent.

In yet another aspect, embodiments disclosed herein relate to a process for producing an ethylene vinyl acetate copolymer that includes polymerizing ethylene at least partially obtained from a renewable source of carbon with vinyl acetate to produce the ethylene vinyl acetate copolymer.

In yet another aspect, embodiments disclosed herein relate to a process for producing an ethylene vinyl acetate copolymer that includes fermenting a renewable source of carbon to produce ethanol; dehydration of ethanol to produce ethylene; and polymerizing ethylene and vinyl acetate to produce the ethylene vinyl acetate copolymer.

Other aspects and advantages of the claimed subject matter will be apparent from the following description and the appended claims.

DETAILED DESCRIPTION

Figure 1:
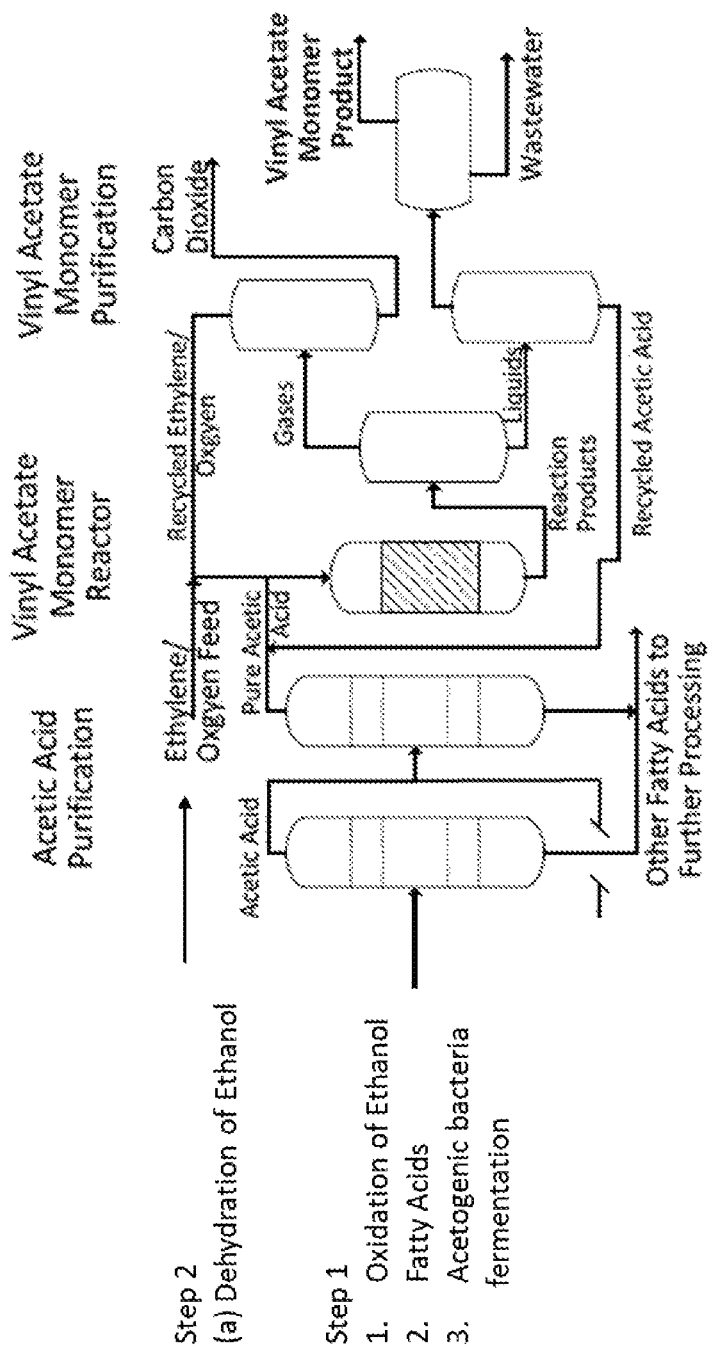
FIG. 1 is an exemplary route for the production of bio-based vinyl acetate according to one or more embodiments of the present disclosure.

In one aspect, embodiments disclosed herein relate to compositions containing ethylene vinyl acetate (EVA) copolymers that have at least a portion of the ethylene thereof that is obtained from a renewable source of carbon, such as a plant-based material, i.e., forming a bio-based ethylene vinyl acetate copolymer EVA is a copolymer of the polyolefin family of elastomers formed by the sequence of random units derived from the polymerization of ethylene and vinyl acetate at high temperature and pressure. EVA copolymers provide materials that can be processed like other thermoplastics, but may offer a rubbery character having softness and elasticity. Further, EVA copolymers may be used in a wide range of applications, such as adhesives, films, expanded articles, etc. The use of products derived from natural sources, as opposed to those obtained from fossil sources, has increasingly been widely preferred as an effective means of reducing the increase in atmospheric carbon dioxide concentration, therefore effectively limiting the expansion of the greenhouse effect. Products thus obtained from natural raw materials have a difference, relative to fossil sourced products, in their renewable carbon contents. This renewable carbon content can be certified by the methodology described in the technical ASTM D 6866-18 Norm, "Standard Test Methods for Determining the Biobased Content of Solid, Liquid, and Gaseous Samples Using Radiocarbon Analysis". Products obtained from renewable natural raw materials have the additional property of being able to be incinerated at the end of their life cycle and only producing $CO_2$ of a non-fossil origin.

Polymer compositions in accordance with the present disclosure may include an EVA copolymer, wherein the percent by weight of ethylene in the EVA polymer ranges from a lower limit selected from one of 5 wt %, 25 wt %, 40 wt %, 60 wt %, 66 wt %, and 72 wt %, to an upper limit selected from one of 80 wt %, 85 wt %, 88 wt %, 92 wt %, and 95 wt %, where any lower limit may be paired with any upper limit. Further, of this total amount of ethylene, it is understood that at least a portion of that ethylene is based on a renewable carbon source.

Polymer compositions in accordance with the present disclosure may include EVA copolymers incorporating various ratios of ethylene and vinyl acetate, in addition to including one or more optional additional comonomers. Polymer compositions in accordance with the present disclosure may include an EVA copolymer, wherein the percent by weight of vinyl acetate content as determined by ASTM D5594 in the copolymer ranges from a lower limit selected from one of 5 wt %, 8 wt %, 12 wt %, 15 wt %, 20 wt % to an upper limit selected from 25 wt %, 30 wt %, 35 wt %, 40 wt %, 60 wt %, 75 wt %, or 95 wt %, where any lower limit may be paired with any upper limit. Further, of this total amount of vinyl acetate, it is understood that at least a portion of that vinyl acetate is based on a renewable carbon source.

Specifically, in one or more embodiments, the EVA copolymer exhibits a bio-based carbon content, as determined by ASTM D6866-18 Method B, of at least 5%. Further, other embodiments may include at least 10%, 20%, 40%, 50%, 60%, 80%, or 100% bio-based carbon. As mentioned above, the total bio-based or renewable carbon in the EVA polymer may be contributed from a bio-based ethylene and/or a bio-based vinyl acetate. Each of these are described in turn.

For example, in one or more embodiments, the renewable source of carbon is one or more plant materials selected from the group consisting of sugar cane and sugar beet, maple, date palm, sugar palm, sorghum, American agave, corn, wheat, barley, sorghum, rice, potato, cassava, sweet potato, algae, fruit, materials comprising cellulose, wine, materials comprising hemicelluloses, materials comprising lignin, wood, straw, sugarcane bagasse, sugarcane leaves, corn stover, wood residues, paper, and combinations thereof.

In one or more embodiments, the bio-based ethylene may be obtained by fermenting a renewable source of carbon to produce ethanol, which may be subsequently dehydrated to produce ethylene. Further, it is also understood that the fermenting produces, in addition to the ethanol, byproducts of higher alcohols. If the higher alcohol byproducts are present during the dehydration, then higher alkene impurities may be formed alongside the ethanol. Thus, in one or more embodiments, the ethanol may be purified prior to dehydration to remove the higher alcohol byproducts while in other embodiments, the ethylene may be purified to remove the higher alkene impurities after dehydration.

Thus, biologically sourced ethanol, known as bio-ethanol, is obtained by the fermentation of sugars derived from cultures such as that of sugar cane and beets, or from hydrolyzed starch, which is, in turn, associated with other cultures such as corn. It is also envisioned that the bio-based ethylene may be obtained from hydrolysis-based products of cellulose and hemi-cellulose, which can be found in many agricultural by-products, such as straw and sugar cane husks. This fermentation is carried out in the presence of varied microorganisms, the most important of such being the yeast *Saccharomyces cerevisiae*. The ethanol resulting therefrom may be converted into ethylene by means of a catalytic reaction at temperatures usually above 300° C. A large variety of catalysts can be used for this purpose, such as high specific surface area gamma-alumina. Other examples include the teachings described in U.S. Pat. Nos. 9,181,143 and 4,396,789, which are herein incorporated by reference in their entirety.

Bio-based vinyl acetate, on the other hand, may also be used in one of more embodiments of the EVA copolymer of the present disclosure. Bio-based vinyl acetate may be produced by producing acetic acid by oxidation of ethanol (which may be formed as described above) followed by reaction of ethylene and acetic acid to acyloxylate the ethylene and arrive at vinyl acetate. Further, it is understood that the ethylene reacted with the acetic acid may also be formed from a renewable source as described above.

An exemplary route of obtaining a bio-based vinyl acetate is shown in FIG. 1. As shown, initially, a renewable starting material, including those described above, may be fermented and optionally purified, in order to produce at least one alcohol (either ethanol or a mixture of alcohols including ethanol). The alcohol may be separated into two parts, where the first part is introduced into a first reactor and the second part may be introduced into a second reactor. In the first reactor, the alcohol may be dehydrated in order to produce an alkene (ethylene or a mixture of alkenes including ethylene, depending on whether a purification followed the fermentation) followed by optional purification to obtain ethylene. One of ordinary skill in the art may appreciate that if the purification occurs prior to dehydration, then it need not occur after dehydration, and vice versa. In the second reactor, the alcohol may be oxidized in order to obtain acetic acid, which may optionally be purified. In a third reactor, the ethylene produced in the first reactor and the acetic acid produced in the second reactor may be combined and reacted to acyloxylate the ethylene and form vinyl acetate, which may be subsequently isolated and optionally purified. Additional details about oxidation of ethanol to form acetic acid may be found in U.S. Pat. No. 5,840,971 and Selective catalytic oxidation of ethanol to acetic acid on dispersed Mo—V—Nb mixed oxides. Li X, Iglesia E. Chemistry. 2007; 13(33):9324-30.

However, the present disclosure is not so limited in terms of the route of forming acetic acid. Rather, it is also envisioned, as indicated in FIG. 1, that acetic acid may be obtained from a fatty acid, as described in "The Production of Vinyl Acetate Monomer as a Co-Product from the Non-Catalytic Cracking of Soybean Oil", Benjamin Jones, Michael Linnen, Brian Tande and Wayne Seames, Processes, 2015, 3, 61-9-633. Further, the production of acetic acid from fermentation performed by acetogenic bacteria, as described in "Acetic acid bacteria: A group of bacteria with versatile biotechnological applications", Saichana N, Matsushita K, Adachi 0, Frébort I, Frebortova J. Biotechnol Adv. 2015 Nov. 1; 33(6 Pt 2):1260-71 and Biotechnological applications of acetic acid bacteria. Raspor P, Goranovic D. Crit Rev Biotechnol. 2008; 28(2):101-24. Further, it is also understood that while FIG. 1 is directed to the formation of vinyl acetate, the production of ethylene used to produce vinyl acetate can also be used to form the ethylene that is subsequently reacted with the vinyl acetate to form the EVA copolymer of the present disclosure. Thus, for example, the amount of ethanol that is fed to the first and second reactors, respectively, may be vary depending on the relative amounts of ethylene and vinyl acetate being polymerized.

Polymer compositions in accordance with the present disclosure may include an EVA copolymer, wherein the number average molecular weight (Mn) in kilodaltons (kDa) of the EVA copolymer ranges from a lower limit selected from one of 5 kDa, 10 kDa, 20 kDa and 25 kDa to an upper limit selected from one of 30 kDa, 35 kDa, 40 kDa and 50 kDa, where any lower limit may be paired with any upper limit.

Polymer compositions in accordance with the present disclosure may include an EVA copolymer, wherein the weight average molecular weight (Mw) in kilodaltons (kDa) of the EVA copolymer ranges from a lower limit selected from one of 25 kDa, 50 kDa, 70 kDa, 90 kDa and 110 kDa to an upper limit selected from one of 120 kDa, 140 kDa, 150 kDa and 180 kDa, where any lower limit may be paired with any upper limit.

Polymer compositions in accordance with the present disclosure may include an EVA copolymer, wherein the dispersity (Mw/Mn) of the EVA copolymer ranges from a lower limit selected from one of 1.0, 1.5, 3.0 and 4.0 to an upper limit selected from one of 5.0, 6.0, 7.0 and 8.0, where any lower limit may be paired with any upper limit.

The molecular weight properties may be measured by GPC (Gel Permeation Chromatography) experiments. Such experiments may be coupled with triple detection, such as with an infrared detector IRS, a four-bridge capillary viscometer (PolymerChar) and an eight-angle light scattering detector (Wyatt). A set of 4 mixed bed, 13 μm columns (Tosoh) may be used at a temperature of 140° C. The experiments may use a concentration of 1 mg/mL, a flow rate of 1 ml/min, a dissolution temperature and time of 160° C. and 90 minutes, respectively, an injection volume of 200 μL, and a solvent of trichlorium benzene stabilized with 100 ppm of BHT.

Polymer compositions in accordance with the present disclosure may include an EVA copolymer, where the EVA copolymer exhibits a melt index as determined by ASTM D1238 that may range from a lower limit selected from one of 0.1, 1, 2, 5, 10, 20, of 50 to an upper limit selected from one of 50, 100, 200, 300, or 400 g/10 min measured with a load of 2.16 kg at 190° C., where any lower limit may be paired with any upper limit.

Polymer compositions in accordance with the present disclosure may include an EVA copolymer, where the density of the EVA copolymer, as determined by ASTM D792, may range from a lower limit selected from one of 0.91, 0.95, 0.97, or 1.1 g/cm$^3$ to an upper limit selected from one of 1.1, 1.5, 1.9, 1.21 or 1.25 g/cm$^3$, where any lower limit may be paired with any upper limit.

Polymer compositions in accordance with the present disclosure may include an EVA copolymer, where copolymer exhibits a Shore A hardness as determined by ASTM D2240 that may range from a lower limit of any of 60, 65, 70, 75, or 80 to an upper limit of 70, 75, 80, 100 Shore A, where any lower limit may be paired with any upper limit.

Polymer compositions in accordance with the present disclosure may include an EVA copolymer, where copolymer exhibits a Vicat Softening Temperature as determined by ASTM D1525 Method A50 that may range from a lower limit of any of 35 40, 45, 50, or 55 to an upper limit of any of 65, 70, 75, 85, or 90° C., where any lower limit may be paired with any upper limit.

Polymer compositions in accordance with the present disclosure may include an EVA copolymer, where the copolymer exhibits a Mooney viscosity ML (1+4) at 100° C. as determined by ASTM D 1646 in the range of 15 to 50 MU. Such Mooney viscosity may be achieved when the vinyl acetate contact is greater than 50% of the copolymer.

As mentioned, it is also envisioned that the EVA copolymer of the present disclosure may also contain one or more additional comonomers, by reacting an EVA polymer resin, prepolymer, or EVA monomers with one or more additional comonomers, including but not limited to one or more polar monomers, such as those of the type described in PCT/BR2017/050398, which is herein incorporated by reference in its entirety.

Polymer compositions in accordance with the present disclosure may include one or more peroxide agents capable of generating free radicals during polymer processing. For example, peroxide agents may be combined with an EVA resin while reacting the polymer such as during polymerization and/or curing. In one or more embodiments, peroxide agents may include bifunctional peroxides such as benzoyl peroxide; dicumyl peroxide; di-tert-butyl peroxide; 00-Tert-amyl-0-2-ethylhexyl monoperoxycarbonate; tert-butyl cumyl peroxide; tert-butyl 3,5,5-trimethylhexanoate peroxide; tert-butyl peroxybenzoate; 2-ethylhexyl carbonate tert-butyl peroxide; 2,5-dimethyl-2,5-di (tert-butylperoxide) hexane; 1,1-di (tert-butylperoxide)-3,3,5-trimethylcyclohexane; 2,5-dimethyl-2,5-di(tert-butylperoxide) hexyne-3; 3,3,5,7,7-pentamethyl-1,2,4-trioxepane; butyl 4,4-di (tert-butylperoxide) valerate; di (2,4-dichlorobenzoyl) peroxide; di(4-methylbenzoyl) peroxide; peroxide di(tert-butylperoxyisopropyl) benzene; and the like.

Peroxide agents may also include benzoyl peroxide, 2,5-di(cumylperoxy)-2,5-dimethyl hexane, 2,5-di(cumylperoxy)-2,5-dimethyl hexyne-3,4-methyl-4-(t-butylperoxy)-2-pentanol, butyl-peroxy-2-ethyl-hexanoate, tert-butyl peroxypivalate, tertiary butyl peroxyneodecanoate, t-butyl-peroxy-benzoate, t-butyl-peroxy-2-ethyl-hexanoate, 4-methyl-4-(t-amylperoxy)-2-pentanol, 4-methyl-4-(cumylperoxy)-2-pentanol, 4-methyl-4-(t-butylperoxy)-2-pentanone, 4-methyl-4-(t-amylperoxy)-2-pentanone, 4-methyl-4-(cumylperoxy)-2-pentanone, 2,5-dimethyl-2,5-di(t-butylperoxy)hexane, 2,5-dimethyl-2,5-di(t-amylperoxy) hexane, 2,5-dimethyl-2,5-di(t-butylperoxy)hexyne-3,2,5-dimethyl-2,5-di(t-amylperoxy)hexyne-3,2,5-dimethyl-2-t-butylperoxy-5-hydroperoxyhexane, 2,5-dimethyl-2-cumylperoxy-5-hydroperoxy hexane, 2,5-dimethyl-2-t-amylperoxy-5-hydroperoxyhexane, m/p-alpha, alpha-di[(t-butylperoxy)isopropyl]benzene, 1,3,5-tris(t-butylperoxyisopropyl)benzene, 1,3,5-tris(t-amylperox- yisopropyl) benzene, 1,3,5-tris(cumylperoxyisopropyl)benzene, di[1,3-dimethyl-3-(t-butylperoxy)butyl]carbonate, di[1,3-dimethyl-3-(t-amylperoxy) butyl]carbonate, di[1,3-dimethyl-3-(cumylperoxy)butyl]carbonate, di-t-amyl peroxide, t-amyl cumyl peroxide, t-butyl-isopropenylcumyl peroxide, 2,4,6-tri(butylperoxy)-s-triazine, 1,3,5-tri[1-(t-butylperoxy)-1-methylethyl]benzene, 1,3,5-tri-[(t-butylperoxy)-isopropyl] benzene, 1,3-dimethyl-3-(t-butylperoxy)butanol, 1,3-dimethyl-3-(t-amylperoxy)butanol, di(2-phenoxyethyl) peroxydicarbonate, di(4-t-butylcyclohexyl)peroxydicarbonate, dimyristyl peroxydicarbonate, dibenzyl peroxydicarbonate, di(isobornyl)peroxydicarbonate, 3-cumylperoxy-1,3-dimethylbutyl methacrylate, 3-t-butylperoxy-1,3-dimethylbutyl methacrylate, 3-t-amylperoxy-1,3-dimethylbutyl methacrylate, tri(1,3-dimethyl-3-t-butylperoxy butyloxy)vinyl silane, 1,3-dimethyl-3-(t-butylperoxy)butyl N-[1-3-(1-methylethenyl)-phenyl) 1-methylethyl]carbamate, 1,3-dimethyl-3-(t-amylperoxy) butyl N-[1-{3(1-methylethenyl)-phenyl}-1-methylethyl] carbamate, 1,3-dimethyl-3-(cumylperoxy))butyl N-[1-{3-(1-methylethenyl)-phenyl}-1-methylethyl]carbamate, 1,1-di (t-butylperoxy)-3,3,5-trimethylcyclohexane, 1,1-di(t-butylperoxy)cyclohexane, n-butyl 4,4-di(t-amylperoxy) valerate, ethyl 3,3-di(t-butylperoxy)butyrate, 2,2-di(t-amylperoxy)propane, 3,6,6,9,9-pentamethyl-3-ethoxycabonylmethyl-1,2,4,5-tetraoxacyclononane, n-buty 1-4,4-bis(t-butylperoxy)valerate, ethyl-3,3-di(t-amylperoxy)butyrate, benzoyl peroxide, OO-t-butyl-O-hydrogen-monoperoxy-succinate, OO-t-amyl-O-hydrogen-monoperoxy-succinate, 3,6,9, triethyl-3,6,9-trimethyl-1,4,7-triperoxynonane (or methyl ethyl ketone peroxide cyclic trimer), methyl ethyl ketone peroxide cyclic dimer, 3,3,6,6, 9,9-hexamethyl-1,2,4,5-tetraoxacyclononane, 2,5-dimethyl-2,5-di(benzoylperoxy)hexane, t-butyl perbenzoate, t-butylperoxy acetate, t-butylperoxy-2-ethyl hexanoate, t-amyl perbenzoate, t-amyl peroxy acetate, t-butyl peroxy isobutyrate, 3-hydroxy-1,1-dimethyl t-butyl peroxy-2-ethyl hexanoate, OO-t-amyl-O-hydrogen-monoperoxy succinate, OO-t-butyl-O-hydrogen-monoperoxy succinate, di-t-butyl diperoxyphthalate, t-butylperoxy (3,3,5-trimethylhexanoate), 1,4-bis(t-butylperoxycarbo)cyclohexane, t-butylperoxy-3,5,5-trimethylhexanoate, t-butyl-peroxy-(cis-3-carboxy)propionate, allyl 3-methyl-3-t-butylperoxy butyrate, OO-t-butyl-O-isopropylmonoperoxy carbonate, OO-t-butyl-O-(2-ethyl hexyl)monoperoxy carbonate, 1,1,1-tris[2-(t-butylperoxy-carbonyloxy)ethoxymethyl]propane, 1,1,1-tris [2-(t-amylperoxy-carbonyloxy)ethoxymethyl]propane, 1, 1, 1-tris[2-(cumylperoxy-cabonyloxy)ethoxymethyl]propane, OO-t-amyl-O-isopropylmonoperoxy carbonate, di(4-methylbenzoyl)peroxide, di(3-methylbenzoyl)peroxide, di(2-methylbenzoyl)peroxide, didecanoyl peroxide, dilauroyl peroxide, 2,4-dibromo-benzoyl peroxide, succinic acid peroxide, dibenzoyl peroxide, di(2,4-dichloro-benzoyl)peroxide, and combinations thereof.

In one or more embodiments, polymer compositions in accordance with the present disclosure may contain a percent by weight of the total composition (wt %) of one or more peroxide agents that ranges from a lower limit selected from one of 0.01 wt %, 0.1 wt %, 0.15 wt %, 0.4 wt %, 0.6 wt %, 0.75 wt % and 1 wt %, to an upper limit selected from one of 0.5 wt %, 1.25 wt %, 2 wt %, 4 wt %, and 5 wt %, where any lower limit can be used with any upper limit. Further, it is envisioned that the concentration of the peroxide agent may be more or less depending on the application of the final material.

It is also envisioned that crosslinking co-agent may be combined in the polymer composition during the curing processes. Crosslinking co-agents create additional reactive sites for crosslinking. Therefore, the degree of polymer crosslinking may be considerably increased from that normally obtained by greater additions of peroxide. Generally co-agents increase the rate of crosslinking. In one or more embodiments, the crosslinking co-agents may include Triallyl isocyanurate (TAIL), trimethylolpropane-tris-methacrylate (TRIM), triallyl cyanurate (TAC) and combinations thereof.

In one or more embodiments, polymeric compositions in accordance with the present disclosure may contain one or more crosslinking co-agent at a parts per hundred resin (phr) that ranges from a lower limit selected from one of 0.01 phr, 0.25 phr, 0.5 phr, 1 phr to an upper limit selected from one of 1.5 phr and 2 phr.

Polymeric compositions in accordance with the present disclosure may include one or more blowing agents to produce expanded polymeric compositions and foams. Blowing agents may include solid, liquid, or gaseous blowing agents. In embodiments utilizing solid blowing agents, blowing agents may be combined with a polymer composition as a powder or granulate.

Blowing agents in accordance with the present disclosure include chemical blowing agents that decompose at polymer processing temperatures, releasing the blowing gases such as $N_2$, CO, $CO_2$, and the like. Examples of chemical blowing agents may include organic blowing agents, including hydrazines such as toluenesulfonyl hydrazine, hydrazides such as oxydibenzenesulfonyl hydrazide, diphenyl oxide-4,4'-disulfonic acid hydrazide, and the like, nitrates, azo compounds such as azodicarbonamide, cyanovaleric acid, azobis(isobutyronitrile), and N-nitroso compounds and other nitrogen-based materials, and other compounds known in the art.

Inorganic chemical blowing agents may include carbonates such as sodium hydrogen carbonate (sodium bicarbonate), sodium carbonate, potassium bicarbonate, potassium carbonate, ammonium carbonate, and the like, which may be used alone or combined with weak organic acids such as citric acid, lactic acid, or acetic acid.

In one or more embodiments, polymeric compositions in accordance with the present disclosure may contain one or more blowing agents at a parts per hundred resin (phr) that ranges from a lower limit selected from one of 1 phr, 1.5 phr, 2 phr, 2.5 phr and 3 phr, to an upper limit selected from one of 3.5 phr, 4 phr, 4.5 phr, 5 phr, 5.5 phr and 6 phr, where any lower limit can be used with any upper limit.

Polymeric compositions in accordance with the present disclosure may include one or more blowing accelerators (also known as kickers) that enhance or initiate the action of a blowing agent by lower the associated activation temperature. For example, blowing accelerators may be used if the selected blowing agent reacts or decomposes at temperatures higher than 170° C., such as 220° C. or more, where the surrounding polymer would be degraded if heated to the activation temperature. Blowing accelerators may include any suitable blowing accelerator capable of activating the selected blowing agent. In one or more embodiments, suitable blowing accelerators may include cadmium salts, cadmium-zinc salts, lead salts, lead-zinc salts, barium salts, barium-zinc (Ba—Zn) salts, zinc oxide, titanium dioxide, triethanolamine, diphenylamine, sulfonated aromatic acids and their salts, and the like.

In one or more embodiments, polymeric compositions in accordance with the present disclosure may contain one or more blowing accelerators at a parts per hundred resin (phr) that ranges from a lower limit selected from one of 0.1 phr, 0.25 phr, 0.5 phr, 1 phr, 2 phr, and 2.5 phr, to an upper limit selected from one of 1.5 phr, 2 phr, 2.5 phr, 3 phr, 3.5 phr, 4 phr, 4.5 phr and 5 phr, where any lower limit can be used with any upper limit.

Additives

Polymer compositions in accordance with the present disclosure may include fillers and additives that modify various physical and chemical properties when added to the polymer composition during blending that include one or more polymer additives such as processing aids, lubricants, antistatic agents, clarifying agents, nucleating agents, beta-nucleating agents, slipping agents, antioxidants, compatibilizers, antacids, light stabilizers such as HALS, IR absorbers, whitening agents, inorganic fillers, organic and/or inorganic dyes, anti-blocking agents, processing aids, flame-retardants, plasticizers, biocides, adhesion-promoting agents, metal oxides, mineral fillers, glidants, oils, antioxidants, antiozonants, accelerators, and vulcanizing agents.

Polymer compositions in accordance with the present disclosure may include one or more inorganic fillers such as talc, glass fibers, marble dust, cement dust, clay, carbon black, feldspar, silica or glass, fumed silica, silicates, calcium silicate, silicic acid powder, glass microspheres, mica, metal oxide particles and nanoparticles such as magnesium oxide, antimony oxide, zinc oxide, inorganic salt particles and nanoparticles such as barium sulfate, wollastonite, alumina, aluminum silicate, titanium oxides, calcium carbonate, polyhedral oligomeric silsesquioxane (POSS), or recycled EVA. As defined herein, recycled EVA may be derived from regrind materials that have undergone at least one processing method such as molding or extrusion and the subsequent sprue, runners, flash, rejected parts, and the like, are ground or chopped.

In one or more embodiments, polymer compositions in accordance with the present disclosure may contain a percent by weight of the total composition (wt %) of one or more fillers that ranges from a lower limit selected from one of 0.02 wt %, 0.05 wt %, 1.0 wt %, 5.0 wt %, 10.0 wt %, 15.0 wt %, and 20.0 wt %, to an upper limit selected from one of 25.0 wt %, 30.0 wt %, 40.0 wt %, 50.0 wt %, 60.0 wt %, and 70.0 wt %, where any lower limit can be used with any upper limit.

In-Reactor Synthesis

In one or more embodiments, polymer compositions in accordance with the present disclosure may be prepared in reactor. Ethylene and vinyl acetate are added in a reactor to polymerize. In some embodiments, the ethylene and vinyl acetate, and optionally one or more polar comonomers, are polymerized by high pressure radical polymerization, wherein peroxide agents act as polymerization initiators. In some embodiments, the ethylene and the vinyl acetate, and the peroxide agents are added at elevated pressure into an autoclave or tubular reactor at a temperature of between 80° C. and 300° C. and a pressure inside the reactor between 500 bar and 3000 bar in some embodiments, and a pressure between 1000 bar and 2600 bar in some embodiments. In other embodiments, the copolymers are produced by a solution polymerization process.

In embodiments containing an additional comonomer, such additional comonomer may be added into the reactor with the ethylene and vinyl acetate; however, it is also understood that it could be reacted with a formed EVA copolymer such as during a reactive extrusion.

As mentioned, one or more free-radical producing agents, including any of those described above may be present during the polymerization.

Post-Polymerization Processes

Further, it is also understood that the EVA copolymer may also be cured, for example in the presence of peroxides as well, including those discussed above and optionally a crosslinking co-agent. For embodiments which include expanded compositions, discussed below, the expanding and curing may be in the presence of a blowing agent and a peroxide agent, and optionally, a kicker and/or a crosslinking co-agent. During any of such curing steps (expanded or not), in one or more embodiments, the curing of the EVA copolymer may occur in full or partial presence of oxygen, such as described in WO201694161A1, which is incorporated by reference in its entirety.

Physical Properties

A cured non-expanded article that includes the EVA copolymer of the present disclosure may have a density as determined by ASTM D-792 that may range of a lower limit of any of 0.7, 0.8, 0.9, or 1.0 to an upper limit of any of 1.0, 1.1, or 1.2 $g/cm^3$, where any lower limit can be used with any upper limit.

Cured non-expanded articles prepared by the polymer compositions in accordance with the present disclosure may have a Shore A hardness as determined by ASTM D2240 within a range having a lower limit selected from one of 40, 50, or 60 Shore A, to an upper limit selected from one of 60, 70, 80, and 90 Shore A, where any lower limit may be paired with any upper limit.

Cured non-expanded articles prepared by the polymer compositions in accordance with the present disclosure may have an abrasion resistance as determined by ISO 4649:2017 measured with a load of 10N within a range having a lower limit selected from one of 20, 40, 60 $mm^3$, 70 $mm^3$, 90 $mm^3$, or 100 $mm^3$, to an upper limit selected from one of 120 $mm^3$, 140 $mm^3$, 170 $mm^3$, 200 $mm^3$, where any lower limit may be paired with any upper limit.

Further, as mentioned, it is also envisioned that the EVA copolymer may be expanded and cured, such as with the described blowing agent and peroxide agent. Expanded articles prepared by the polymer compositions in accordance with the present disclosure may have a density as determined by ASTM D-792 within a range having a lower limit selected from one of 0.05 $g/cm^3$, 0.12 $g/cm^3$, 0.2 $g/cm^3$, 0.25 $g/cm^3$, 0.5 $g/cm^3$, to an upper limit selected from one of 0.4 $g/cm^3$, 0.5 $g/cm^3$, 0.6 $g/cm^3$, 0.65 $g/cm^3$, and 0.70 $g/cm^3$, where any lower limit may be paired with any upper limit.

Expanded articles prepared by the polymer compositions in accordance with the present disclosure may have an Asker C hardness as determined by ABNT NBR 14455:2015 in the range having a lower limit of any of 20, 30, 40 or 50 Asker C and an upper limit of any 50, 60, 70, or 95 Asker C, where any lower limit can be paired with any upper limit.

Expanded articles prepared by the polymer compositions in accordance with the present disclosure may have a permanent compression set (PCS) as determined by ASTM D395:2016 Method B within a range having a lower limit selected from one of 20%, 30%, 40%, or 50% to an upper limit selected from one of 50%, 60%, 70%, 80% or 90% where any lower limit may be paired with any upper limit.

Expanded articles prepared by the polymer compositions in accordance with the present disclosure may have a rebound as determined by ABNT NBR 8619:2015 within a range having a lower limit selected from one of 20%, 30%, 35%, 40%, 45%, and 50% to an upper limit selected from one of 50%, 60%, 70%, 80% and 90%, where any lower limit may be paired with any upper limit.

Expanded articles prepared by the polymer compositions in accordance with the present disclosure may have a shrinkage at 70° C.*1 h using the PFI method (PFI "Testing and Research Institute for the Shoe Manufacturing Industry" in Pirmesens-Germany) within a range having a lower limit selected from one of 0.1%, 1%, 1.5%, and 5% to an upper limit selected from one of 4%, 5%, 6%, and 7%, where any lower limit may be paired with any upper limit.

The PFI method may be used in the industry for shrinkage measurements and is detailed below:
Equipment:
oven with forced air circulation
pachymeter
ruler for marking of specimens or template
thickness gauge Sample Three specimens of dimensions of at least 100×100 mm should be evaluated of each sample.

Procedure

The specimens may be conditioned at a temperature of 23±2° C. and a relative humidity of 50±5% for 1 hour. The approximate thickness of the specimens is measured.

Figure 2:
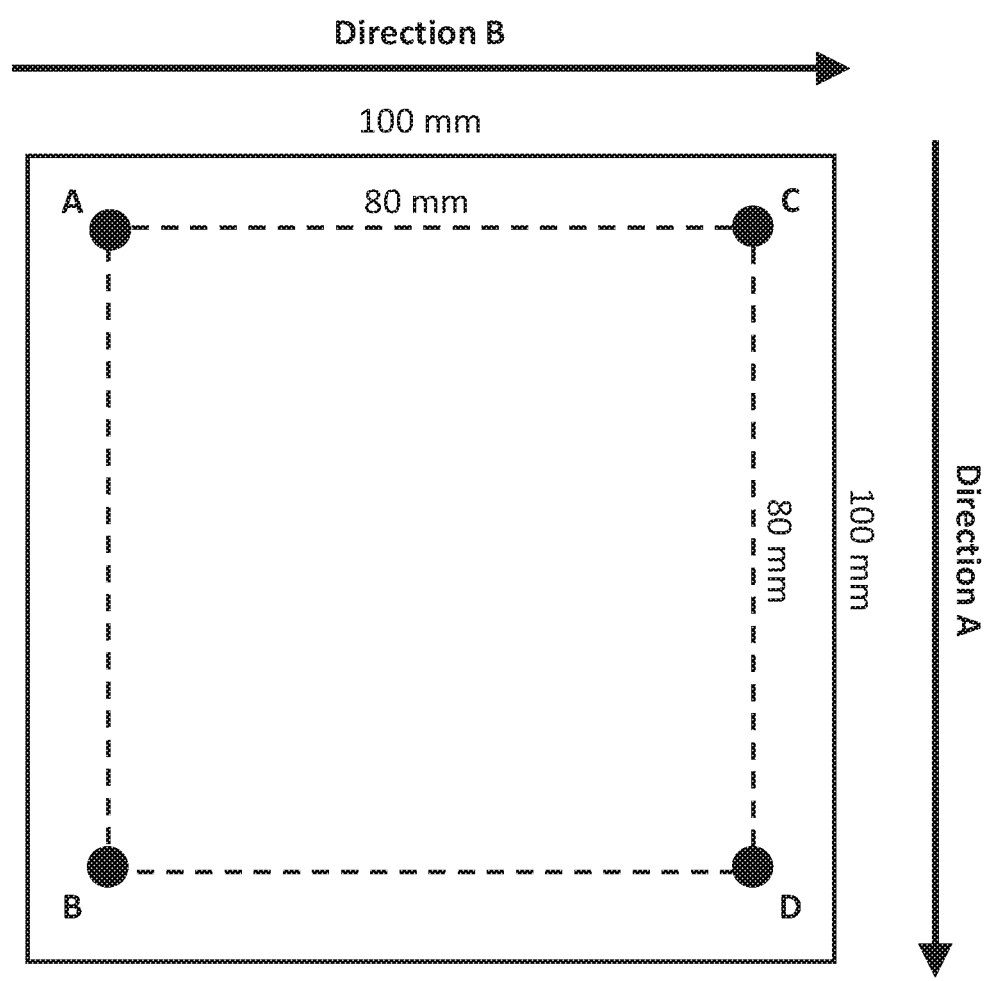
FIG. 2 depicts various points pertinent to the PFI method of determining article shrinkage according to one or more embodiments of the present disclosure.

Using a ruler or template, the points A, B, C and D are marked on each of the specimens as shown in FIG. 2.

The initial length ($C_i$) is measured with a pachymeter, to the nearest 0.01 mm, in direction A (segments A-B and C-D) and in the direction B (segments A-C and B-D).

The specimens are then held at 70° C. for 1 hour in a forced air circulation oven.

After the exposure period, the specimens are removed from the oven and conditioned at a temperature of 23±2° C. and a relative humidity of 50±5% for 60 minutes.

The final length ($C_f$) is measured with a caliper, to the nearest 0.01 mm, in direction A (segments A-B and C-D) and direction B (segments A-C and B-D).

The average initial length ($C_{im}$) is calculated in the A direction as the average of the A-B and C-D segments and in the B direction as the average of the A-C and B-D segments for each of the specimens.

The average final length ($C_{fm}$) is calculated in the A direction as the average of the A-B and C-D segments and the B direction as the average of the A-C and B-D segments for each of the specimens.

Results

The shrinkage of the expanded EVA is given by the following equation, expressed as a percentage to the nearest 0.1%.

$$\text{Shrinkage \%} = (C_{im} - C_{fm}) \times 100 / C_{im}$$

Where:
$C_{im}$=initial length average (mm)
$C_{fm}$=final length average (mm)
The final EVA shrinkage result will be calculated for the directions A and B as the average of the shrinkage values calculated for each specimen.

Note: The PFI recommends acceptable maximum values for shrinkage of expanded materials in directions A and B (FIG. 1):

3% for materials with a density up to 0.6 g/cm$^3$
2% for materials with a density above 0.6 g/cm$^3$ Expanded articles prepared by the polymer compositions in accordance with the present disclosure may have an abrasion resistance as determined by ISO 4649 measured with a load of 5N within a range having a lower limit selected from one of 40, 80, 120 mm$^3$, 150 mm$^3$, 200 mm$^3$, or 400 mm$^3$, to an upper limit selected from one of 300 mm$^3$, 600 mm$^3$, 700 mm$^3$, 800 mm$^3$, where any lower limit may be paired with any upper limit.

Applications

In one or more embodiments, polymer compositions can be used in various molding processes, including extrusion molding, compression molding, injection molding, thermoforming, cast film extrusion, blown film extrusion, foaming, extrusion blow-molding, injection blow-molding, ISBM (Injection Stretched Blow-Molding), 3D printing, rotomolding, pultrusion, double expansion process and the like, to produce manufactured articles.

Polymer compositions in accordance with the present disclosure may be used to generate adhesive films for fabrics and non-woven materials including fabric, non-woven, polyurethane, EVA, polypropylene, polyethylene, polyvinylchloride polymer, polyester, polyamide, and the like. In some embodiments, polymer compositions may be incorporated into an adhesive film that is used to form a multi-layer article containing one or more adhesive layers and one or more substrate layers that include the fabrics and non-wovens. Substrate layers may take the form of films, blocks, or sheets in various embodiments. In particular embodiments where the EVA copolymer is present as a film, the polymer may be selected from a narrower melt index and vinyl acetate content in the range that is present above. For example, the melt index selected may range from a narrow range of 1 to 6 g/10 min, with a vinyl acetate content of 5 to 19 wt %; however, it is also recognized that a higher vinyl acetate content may be aligned with a different melt-flow index Films prepared from polymer compositions may be suitable for dubbing woven and non-woven fabrics (NWF) obtained from natural fibers such as cotton and wool, or synthetic fibers such as polyesters and polyolefins including polypropylene. In one or more embodiments, an adhesive film comprising the EVA of the present disclosure may be used in a multi-layer article, where the adhesive film may be applied to a substrate such as a film, sheet, or block, for example. Thus, for example in particular embodiments, the multilayer article of the present disclosure may include at least one layer of the bio-based EVA with at least a second layer that may be a substrate made by materials selected from fabric, non-wovens, polyurethane, another EVA, polypropylene, polyethylene, polyvinylchloride polymer, polyester, and polyamide, for example.

In one or more embodiments, polymer compositions may be formulated as an adhesive composition that possesses a maximum adhesive strength measured according to ABNT NBR 10456:2012 of greater than 20 N. In some embodiments, polymer compositions may exhibit an adhesive strength of greater than 30 N. For example, the maximum adhesive strength may be in a range of 20 N to 50 N.

Polymer compositions in accordance with the present disclosure may also be formulated for a number of polymer articles, including the production of insoles, midsole, soles, hot-melt adhesives, primers, in civil construction as linings, industrial floors, acoustic insulation. Polymeric compositions in accordance with the present disclosure may be formed into articles used for a diverse array of end-uses including shoe soles, midsoles, outsoles, unisoles, insoles, monobloc sandals and flip flops, full EVA footwear, sportive articles, and the like. In particular embodiments, such articles may have a vinyl content that is at least 17 wt %, such as in the range of 18 to 40 wt %.

Other applications may include seals, hoses, gaskets, foams, foam mattresses, furniture, electro-electronic, automotive, packaging, EVA tires, bras, mats, paperboards, sportive articles, toys, swimming accessories, legs floats, yoga blocks, dumbbell gloves, gym steps, rodo sheets, kimono strips, sandpapers, finger protectors, wall protectors, finger separators, educational games and articles, decorative panels, EVA balls, twisted Hex stools, slippers, pillow, sponges, seats, cycling bib pad, protective covers, carpets, aprons and others.

In one or more embodiments, modified EVA compositions may be formulated as a concentrated masterbatch for the production of blends with other resins. Masterbatch compositions may then be combined with other polymers to generate a polymer working stock. The mixture for obtaining the blend may be carried out in any conventional mixing process of resins, such as the solubilization and extrusion processes discussed above. In one or more embodiments, polymer compositions may be formulated as a masterbatch that is added at a percent by weight of 1 wt % to 20 wt % to a polymer resin to create a working stock.

Polymeric Resin

In one or more embodiments, polymer compositions may include other polymeric resins in addition to the EVA copolymer of the present disclosure. In some embodiments, one or more biobased EVA copolymers may be combined with petrochemical based polymers, such as petrochemical EVA.

In some embodiments, a masterbatch formulation may be prepared from an EVA resin (or ethylene and vinyl acetate monomers) that is later combined with a polymeric resin to generate a working stock for the production of adhesives or polymer articles. In such a manner, in addition to the use of the EVA as an adhesive, it is also envisioned that the EVA co-polymer of the present disclosure may serve as a compatibilizer for other polymeric resins.

In one or more embodiments, the EVA copolymer may serve as a compatibilizer between incompatible or thermodynamically immiscible polymeric resins to produce blends which exhibit good mechanical properties and processing, for a wide variety of polymeric resins, where the compatibilizer decreases the interfacial tension between the two phases.

Polymeric resins in accordance with the present disclosure include, for example, polyethylene, polyethylene copolymers such as ethylene maleic anhydride and the like, polypropylene, polystyrene, polybutadiene, polyvinylchloride, ethylene-vinyl acetate copolymer (EVA), polyesters such as polyethylene terephthalate (PET), polyhydroxyalkanoate (PHA), high impact polystyrene (HIPS), and acrylonitrile butadiene styrene (ABS), polyurethane, elastomers such as 5-vinyl-2-norbornene-EPDM, polysulfide rubber, ethylene propylene rubber (EPM), poly(ethylene-methyl acrylate), poly(ethylene-acrylate), ethylene propylene diene rubber (EPDM), vinyl silicone rubber (VMQ), fluorosilicone (FVMQ), nitrile rubber (NBR), acrylonitrile-butadiene-styrene (ABS), styrene butadiene rubber (SBR), styrene-butadiene-styrene block copolymers (SBS), styrene-ethylene-butylene-styrene triblock copolymer (SEBS), polybutadiene rubber (BR), styrene-isoprene-styrene block copolymers (SIS), partially hydrogenated acrylonitrile butadiene (HNBR), natural rubber (NR), synthetic polyisoprene rubber (IR), neoprene rubber (CR), polychloropropene, bromobutyl rubber, chlorobutyl rubber, chlorinated poly(ethylene), vinylidene fluoride copolymers (CFM), silicone rubber, vinyl silicone rubber, chlorosulfonated poly(ethylene), fluoroelastomer, elastomeric polyolefins such as ethylene C3-C12 alpha olefin copolymer, and combinations thereof.

In some embodiments, the EVA copolymer may serve as compatibilizer in polyolefins and biopolymer blends. The biopolymers may include, but are not limited to, starch, polysaccharides such as cellulose and methylcellulose, polylactic acid (PLA), polyhydroxyalkanoates (PHA) such as polyhydroxybutyrate (PHB), polyhydroxyvalerate (PHV), polyhydroxyhexanoate (PHH), polyhydroxyoctanoate (PHO) and copolymers thereof, and combinations thereof.

EXAMPLES

In the following examples, polymer compositions formulations were prepared and assayed to study various physical properties.

Example 1—Production of Biobased Copolymer of Ethylene Vinyl Acetate

A biobased copolymer of ethylene and vinyl acetate according to the present invention was prepared using ethylene obtained from the dehydration of ethanol obtained from sugarcane. Dehydration of ethanol to produce ethylene was conducted in a series of four fixed bed adiabatic reactors connected in series with temperature varying from 350° C. to 480° C. and a pressure of 3 to 10 atm, using an alumina catalyst. The reaction product is subsequently purified by cryogenic distillation and a polymer grade ethylene is obtained.

The copolymer of ethylene and vinyl acetate was produced in a high pressure tubular reactor having a 1.110 m length and a 50 mm diameter. The ethylene was injected at a flow rate of 8.5 tonnes/hour into the reactor and vinyl acetate was injected at a flow rate of 2000 kg/hour. The mixture was compressed in a hyper compressor to 2400 bar and preheated at 130° C. A mixture of tertiary-butyl peroxypivalate/t-Butyl Peroxy-2-ethyl-hexanoate/00-Tert-amyl-0-2-ethylhexyl monoperoxycarbonate was used as initiator. The reaction temperature was varied between 190° C. and 250° C., with a production of 8.5 tonnes/hour of EVA copolymer. The table below presents the properties of the resulting biobased EVA.

TABLE 1

Biobased EVA obtained according to the present disclosure

| Properties | Unit | Value |
|---|---|---|
| Vinyl acetate content | wt % | 18.7 |
| Melt Index (190° C. @2.16 kg) | g/10 min | 1.95 |
| Density | g/cm$^3$ | 0.941 |
| Hardness | Shore A | 89 |
| VICAT | ° C. | 64 |
| Biobased carbon content | % | 88 |

Example 2—Preparation of Cured Non-Expanded Articles

In the following example, curable polymeric composition formulations were prepared in a kneader model XSN-5 QUANZHOU YUCHENGSHENG MACHINE CO., LTD at a temperature of 100° C. and subsequently laminated in a cylinder (open-mix) and pressed and cured in a hydraulic press model LPB-100-AQ-EVA from Luxor Indústria de Maquinas Ltda at 175° C. for 7 min to produce plaques of 10×10 cm, which were assayed to study various physical properties. Curable polymeric composition formulations, including a mixture of biobased EVA and petrochemical EVA are shown in Table 2.

TABLE 2

Curable non-expanded polymer compositions

| Material | C1 PHR | C2 PHR |
|---|---|---|
| Biobased EVA prepared in example 1 | 100 | 50 |
| Petrochemical EVA (HM-728 from Braskem) | 0 | 50 |
| Stearic Acid | 1 | 1 |
| Peroxide agent (bis-peroxide 40%) | 1.8 | 1.8 |
| Total | 102.8 | 102.8 |

Samples were assayed for hardness (Shore A), density, abrasion resistance and biobased carbon content, and the results are shown in Table 3.

TABLE 3

Properties of cured non-expanded polymer compositions

| Properties | Unit | C1 | C2 |
|---|---|---|---|
| Hardness Shore A | Shore A | 88 | 85 |
| Density | g/cm$^3$ | 0.943 | 0.948 |
| Abrasion resistance | mm$^3$ | 26 | 51 |
| Biobased carbon content | % | 88 | 47 |

Example 3

Preparation of expanded articles In the following example, expandable polymeric composition formulations were prepared in a kneader model XSN-5 QUANZHOU YUCHENGSHENG MACHINE CO., LTD at a temperature of 105° C. and subsequently laminated in a cylinder (open-mix) and pressed and cured in a hydraulic press model LPB-100-AQ-EVAfrom Luxor Indústria de Maquinas Ltda at 175° C. for 7 min and expanded at different expansion rates to produce plaques, which were assayed to study various physical properties. Exapandable polymeric composition formulations are shown in Table 4.

TABLE 4

Expandable polymer compositions

| Material | C3 PHR | C4 PHR | C5 PHR | C6 PHR |
|---|---|---|---|---|
| Biobased EVA prepared in example 1 | 100 | 100 | 100 | 50 |
| Petrochemical EVA (HM 728 from Braskem) | 0 | 0 | 0 | 50 |
| Calcium Carbonate | 10 | 10 | 10 | 10 |
| Zinc Oxide | 2 | 2 | 2 | 2 |
| Stearic Acid | 1 | 1 | 1 | 1 |
| Blowing Agent (azodicarbonamide) | 1.1 | 1.6 | 3.5 | 1.7 |
| Peroxide agent (bis-peroxide 40%) | 1.7 | 1.7 | 1.7 | 1.7 |
| Total | 115.8 | 116.3 | 118.2 | 116.4 |

Samples were assayed for hardness (Shore A and Asker C), density, abrasion resistance, compression set, shrinkage, rebound and biobased carbon content, and the results are shown in Table 5.

TABLE 5

Properties of expanded polymer compositions

| Properties | Unit | C3 | C4 | C5 | C6 |
|---|---|---|---|---|---|
| Expansion Rate | % | 30 | 50 | 90 | 50 |
| Hardness Asker C | Asker C | 80 | 70 | 48 | 57 |
| Hardness Shore A | Shore A | 64 | 57 | 36 | 41 |
| Density | g/cm$^3$ | 0.379 | 0.319 | 0.141 | 0.247 |
| Abrasion | mm$^3$ | 55 | 78 | 162 | 167 |
| Compression Set | % | 50 | 52 | 44 | 53 |
| Shrinkage | % | 0.25 | 0.25 | 1 | 1.5 |
| Rebound | % | 41 | 41 | 42 | 45 |
| Biobased carbon content | % | 87 | 87 | 87 | 46 |

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed:

1. A copolymer of ethylene and vinyl acetate, in which the ethylene is at least partially obtained from a renewable source of carbon, wherein the copolymer exhibits a Shore A hardness as determined by ASTM D2240 in the range of 60 to 100 Shore A, wherein the copolymer exhibits a biobased carbon content as determined by ASTM D6866-18 Method B of at least 5%, and wherein the copolymer produces a reduced concentration of carbon dioxide having a fossil origin compared to a copolymer exhibiting a biobased carbon content of 0%.

2. The copolymer of claim 1, wherein the vinyl acetate is at least partially obtained from a renewable source of carbon.

3. The copolymer of claim 1, wherein the vinyl acetate is present in the copolymer in an amount ranging from 5 to 95 wt %.

4. The copolymer of claim 1, wherein the ethylene is present in the copolymer in an amount ranging from 5 to 95 wt %.

5. The copolymer of claim 1, wherein the copolymer exhibits a Shore A hardness as determined by ASTM D2240 in the range of 60 to 80 Shore A.

6. The copolymer of claim 1, wherein the copolymer exhibits a Mooney viscosity ML (1+4) at 100° C. as determined by ASTM D 1646 in the range of 15 to 50 MU.

7. The copolymer of claim 1, wherein the copolymer further comprises at least one additional comonomer.

8. The copolymer of claim 1, wherein the copolymer exhibits a biobased carbon content as determined by ASTM D6866-18 Method B of at least 10%.

9. An article prepared from the copolymer of claim 1.

10. A curable polymer composition comprising the copolymer of claim 1 and at least a peroxide agent.

11. A cured non-expanded article prepared from the curable polymer composition of claim 10.

12. The cured non-expanded article of claim 11, wherein the cured article exhibits a density as determined by ASTM D-792 within the range of 0.7 to 1.2 g/cm$^3$.

13. The cured non-expanded article of claim 11, wherein the cured article exhibits a Shore A hardness as determined by ASTM D2240 in the range of 40 to 90 Shore A.

14. The cured non-expanded article of claim 11, wherein the cured article exhibits an abrasion resistance as determined by ISO 4649:2017 measured with a load of 10N within the range 20 mm$^3$ to 200 mm$^3$.

15. The cured non-expanded article of claim 11, wherein the cured article exhibits a biobased carbon content as determined by ASTM D6866-18 Method B of at least 5%.

16. An expandable polymer composition comprising the copolymer of claim 1 and at least a blowing agent and a peroxide agent.

17. An expanded article prepared from the expandable polymer composition of claim 16.

18. The expanded article of claim 17, wherein the expanded article exhibits a density as determined by ASTM D-792 within the range of 0.05 to 0.7 g/cm$^3$.

19. The expanded article of claim 17, wherein the expanded article exhibits an Asker C hardness as determined by ABNT NBR 14455:2015 in the range of 20 to 95 Asker C.

20. The expanded article of claim 17, wherein the expanded article exhibits a permanent compression set as determined by ASTM D395:2016 Method B in the range of 20% to 95%.

21. The expanded article of claim 17, wherein the expanded article exhibits a rebound as determined by ABNT NBR 8619:2015 within the range of 20% to 80%.

22. The expanded article of claim 17, wherein the expanded article exhibits an abrasion resistance as determined by ISO 4649 measured with a load of 5 N within the range 40 mm3 to 400 mm3.

23. The expanded article of claim 17, wherein the expanded article exhibits a shrinkage as determined at 70° C.*1h according to the PFI method between 0.1 and 7%.

24. The expanded article of claim 17, wherein the expanded article exhibits a biobased carbon content as determined by ASTM D6866-18 Method B of at least 5%.

25. The article of claim 9, wherein the article is selected from a group consisting of shoe soles, midsoles, outsoles, unisoles, insoles, monobloc sandals, flip flops, full EVA footwear, sportive articles, seals, hoses, gaskets, foams, foam mattresses and automotive parts.

26. A process for forming an ethylene vinyl acetate copolymer, comprising:
    polymerizing ethylene at least partially obtained from a renewable source of carbon with vinyl acetate to produce the ethylene vinyl acetate co-polymer, the copolymer exhibits a Shore A hardness as determined by ASTM D2240 in the range of 60 to 100 Shore A, wherein the copolymer exhibits a biobased carbon content as determined by ASTM D6866-18 Method B of at least 5%, and wherein the copolymer produces a reduced concentration of carbon dioxide having a fossil origin compared to a copolymer exhibiting a biobased carbon content of 0%.

27. The process of claim 26, wherein the ethylene vinyl acetate copolymer exhibits a biobased carbon content as determined by ASTM D6866-18 Method B of at least 10%.

28. The process of claim 26, wherein the vinyl acetate is at least partially obtained from a renewable source of carbon.

29. The process of claim 26, further comprising:
    fermenting a renewable source of carbon to produce ethanol; and
    dehydrating the ethanol to produce the ethylene.

30. The process of claim 29, wherein the fermenting produces the ethanol and byproducts comprising higher alcohol, and the dehydration produces the ethylene and higher alkene impurities, wherein the process further comprises: purifying ethylene and the higher alkene impurities in order to obtain the ethylene.

31. The process of claim 29, wherein the fermenting produces the ethanol and byproducts comprising higher alcohols, wherein the process further comprises: purifying the ethanol and byproducts in order to obtain the ethanol.

32. The process of claim 29, wherein the renewable source of carbon are plant materials selected from the group consisting of sugar cane and sugar beet, maple, date palm, sugar palm, sorghum, American agave, corn, wheat, barley, sorghum, rice, potato, cassava, sweet potato, algae, fruit, materials comprising cellulose, wine, materials comprising hemicelluloses, materials comprising lignin, wood, straw, sugarcane bagasse, sugarcane leaves, corn stover, wood residues, paper, and combinations thereof.

33. The process of claim 29, wherein the ethylene vinyl acetate copolymer exhibits a biobased carbon content as determined by ASTM D6866-18 Method B of at least 5%.

34. The process of claim 26, wherein the process further comprises: curing the ethylene vinyl acetate copolymer in the presence of a peroxide agent.

35. The process of claim 26, wherein the process further comprises: expanding and curing the ethylene vinyl acetate copolymer in the presence of at least a blowing agent and a peroxide agent.

36. The process of claim 34, wherein the curing of the ethylene vinyl acetate copolymer occurs in a full or partial presence of oxygen.

* * * * *